(12) United States Patent
Ohno et al.

(10) Patent No.: US 7,476,230 B2
(45) Date of Patent: Jan. 13, 2009

(54) INSERTION DEVICE FOR AN INTRAOCULAR LENS

(75) Inventors: Kenichiro Ohno, Kosigaya (JP); Kenichi Shinzaki, Chiba (JP); Takashi Masuda, Tokyo (JP)

(73) Assignee: STAAR Japan Inc., Tokyo (JP)

( * ) Notice: Subject to any disclaimer, the term of this patent is extended or adjusted under 35 U.S.C. 154(b) by 458 days.

(21) Appl. No.: 10/951,339

(22) Filed: Sep. 27, 2004

(65) Prior Publication Data

US 2005/0075646 A1    Apr. 7, 2005

(30) Foreign Application Priority Data

Oct. 1, 2003    (JP) .............................. 2003-343360

(51) Int. Cl.
*A61F 9/00* (2006.01)
(52) U.S. Cl. ...................................... 606/107; 623/6.12
(58) Field of Classification Search ................. 606/107, 606/108, 166; 623/1.11, 1.12, 1.13, 6.12, 623/6.11; 604/6.12, 188; 221/26
See application file for complete search history.

(56) References Cited

U.S. PATENT DOCUMENTS

| | | | | |
|---|---|---|---|---|
| 5,275,604 A | * | 1/1994 | Rheinish et al. ............. | 606/107 |
| 5,474,562 A | * | 12/1995 | Orchowski et al. .......... | 606/107 |
| 5,496,328 A | | 3/1996 | Nakajima et al. | |
| 5,616,148 A | | 4/1997 | Eagles et al. | |
| 5,772,666 A | * | 6/1998 | Feingold et al. ............. | 606/107 |
| 5,876,406 A | * | 3/1999 | Wolf et al. .................. | 606/107 |
| 6,248,111 B1 | * | 6/2001 | Glick et al. ................. | 606/107 |
| 6,251,114 B1 | * | 6/2001 | Farmer et al. ............... | 606/107 |
| 6,355,046 B2 | | 3/2002 | Kikuchi et al. | |
| 2003/0050646 A1 | * | 3/2003 | Kikuchi et al. ............. | 606/107 |
| 2005/0149058 A1 | * | 7/2005 | Lin et al. .................... | 606/107 |

FOREIGN PATENT DOCUMENTS

| | | |
|---|---|---|
| JP | SHO58-146346 | 8/1983 |
| JP | HEI4-212350 | 8/1992 |
| JP | HEI5-103803 | 4/1993 |
| JP | HEI5-103808 | 4/1993 |
| JP | HEI5-103809 | 4/1993 |
| JP | 7-23990 | 1/1995 |
| JP | 7-23991 | 1/1995 |
| JP | 8-38542 | 2/1996 |
| JP | 9-506285 | 6/1997 |
| JP | 11-510711 | 9/1999 |
| JP | 2000-60880 | 2/2000 |
| JP | 2001-104347 | 4/2001 |
| JP | 2003-70829 | 3/2003 |

\* cited by examiner

*Primary Examiner*—Todd E Manahan
*Assistant Examiner*—Thomas McEvoy
(74) *Attorney, Agent, or Firm*—W. Norman Roth (57) ABSTRACT

In an intraocular-lens insertion device for deforming a deformable intraocular lens to a smaller size and inserting the intraocular lens into an eye via an insertion tube, the insertion tube has such an inner wall shape as to cause the deformable intraocular lens to move rotationally about an insertion tube axis by a predetermined angle in the course of axial movement.

6 Claims, 8 Drawing Sheets

(PRIOR ART)

INSERTION DEVICE FOR AN INTRAOCULAR LENS

BACKGROUND OF THE INVENTION

1. Field of the Invention

The present invention relates to an insertion device for a deformable intraocular lens that is inserted into the eye in place of the natural lens when the latter is physically extracted because of cataract, for a deformable sight corrective lens that is inserted into the eye only for the purpose of sight correction, or for a like deformable intraocular lens.

2. Description of the Related Art

In 1949, Ridley became the first to implant an artificial lens; i.e., an intraocular lens, into the human eye in place of the natural lens, which had become cloudy. Since then, implantation of an intraocular lens has been widely practiced as treatment for cataract.

Japanese Patent Application Laid-Open (kokai) No. 58-146346 discloses deformable intraocular lenses that can be inserted into the eye through a small incision formed therein, such as a deformable intraocular lens that uses a deformable, elastic material having predetermined memory characteristics to form at least its optical portion, and a deformable intraocular lens that uses a deformable, elastic material having predetermined memory characteristics to form at least its optical portion and includes supports, which are adapted to support the optical portion within the eye and are made of a material different from that of the optical portion.

As shown in Japanese Patent Application Laid-Open (kokai) No. 4-212350, etc., the assignee of the present invention has proposed an insertion device for implantation of a deformable intraocular lens in the eye through a small incision formed in the eye. In the proposed device, the optical portion of a deformable intraocular lens is deformed to a smaller size before insertion thereof, through an operation of compressing, rolling, bending, stretching, or folding. The invention of such an insertion device has enhanced accuracy of and simplified a surgery for implantation of an intraocular lens in the eye.

Figure 10:
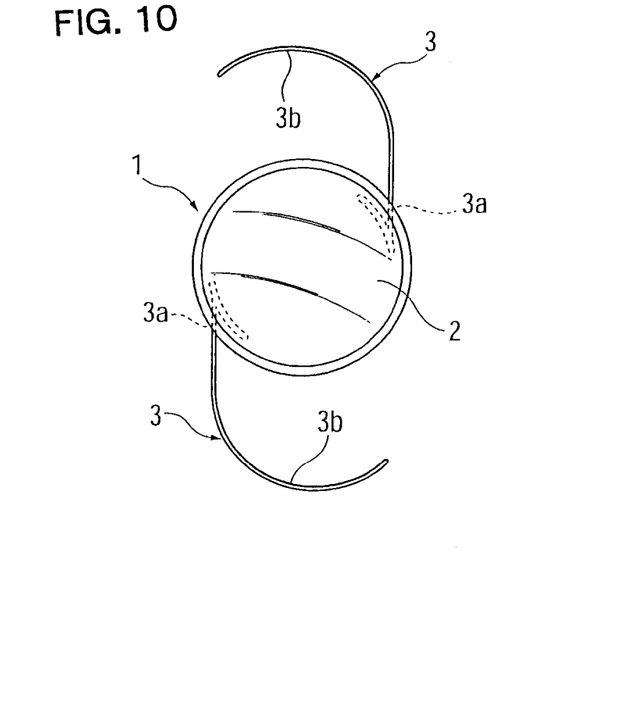
FIG. 10 is an enlarged plan view of a deformable intraocular lens.
Figure 11A:
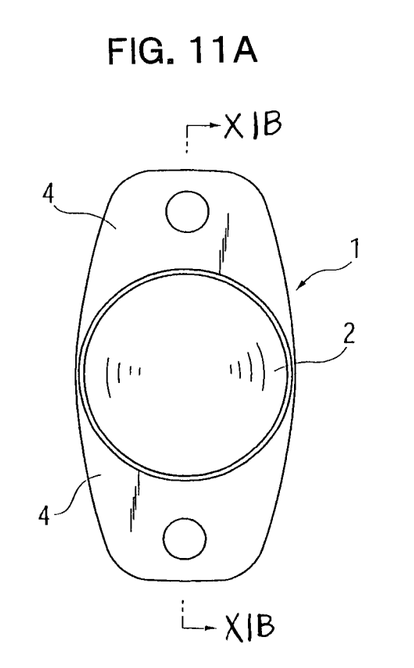
FIG. 11A is an enlarged plan view of another deformable intraocular lens.
Figure 11B:
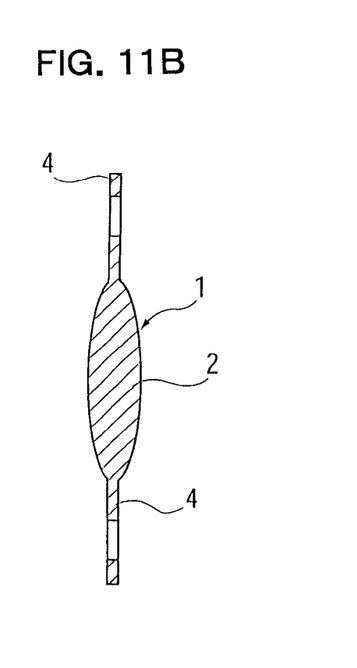
FIG. 11B is a cross-sectional view taken along line XIB-XIB of FIG. 11A.

FIGS. 10 and 11 show examples of deformable intraocular lenses. A deformable intraocular lens 1 shown in FIG. 10 includes a circular, optical portion 2 and a pair of supports 3. The optical portion 2 is made of a deformable, elastic material having predetermined memory characteristics. The supports 3 are made of a flexible material different from that of the optical portion 2. A base end portion 3a of each of the supports 3 is embedded in a circumferential portion of the optical portion 2. A linear projection portion 3b of each of the supports 3 is curved. The paired supports 3 are arranged symmetrically. FIG. 11A, and FIG. 11B, which is a sectional view taken along line XIB-XIB of FIG. 11A, show another deformable intraocular lens 1 made of a material having predetermined memory characteristics similar to that of FIG. 10. Two supports 4 project in opposite directions from a circumferential portion of a circular, optical portion 2.

Figure 12:
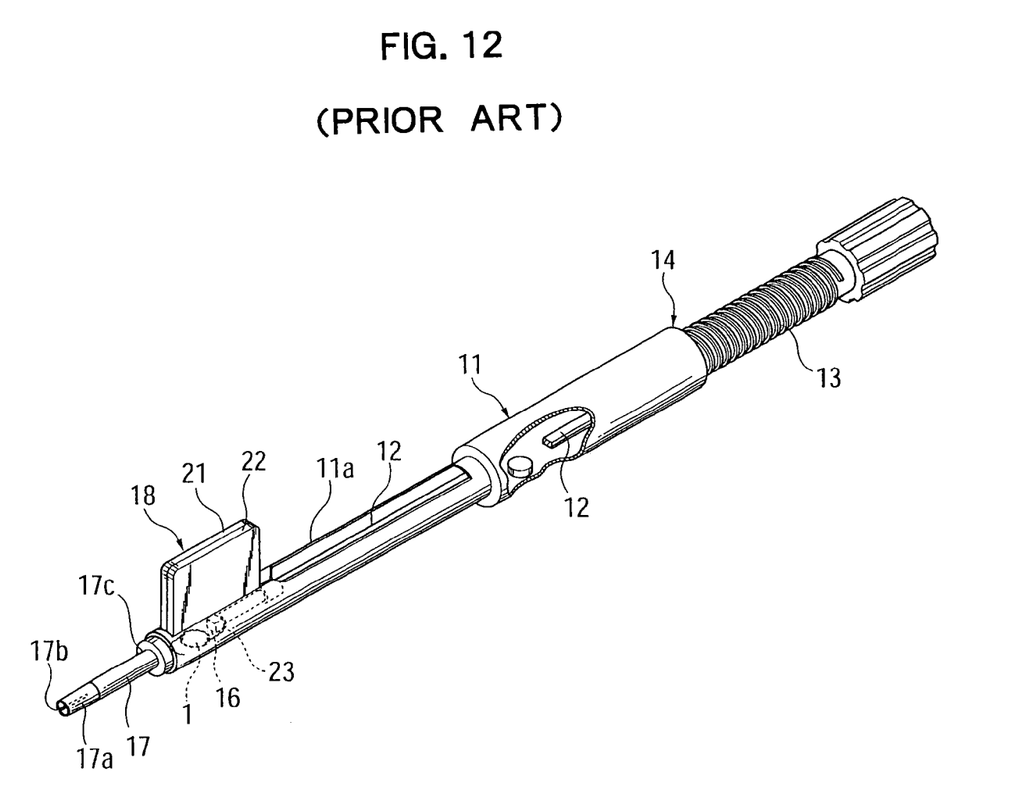
FIG. 12 is a partially cutaway perspective view of a conventional intraocular-lens insertion device.

FIG. 12 is an exterior view of an insertion device for folding either of the above-mentioned deformable intraocular lenses in half and inserting the folded lens into the eye through an insertion tube.

Figure 14:
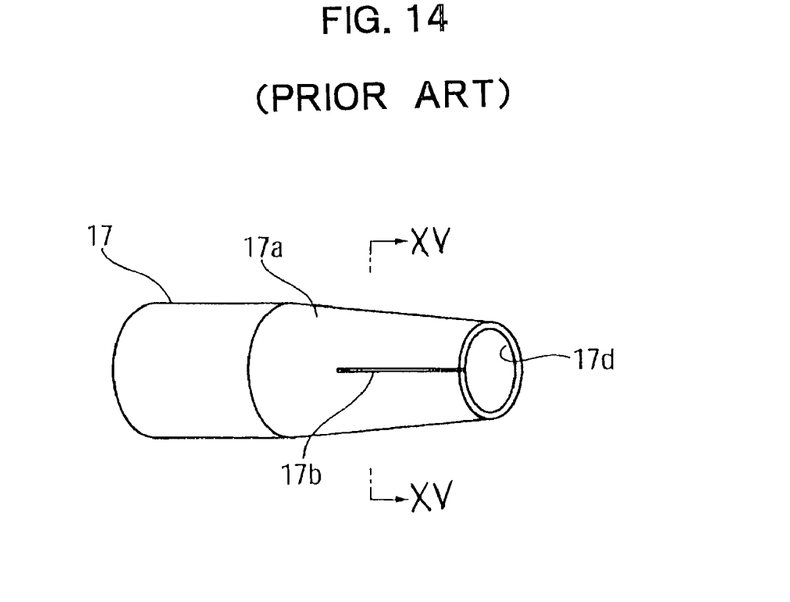
FIG. 14 is an enlarged perspective view of the insertion end portion of FIG. 12.
Figure 15:
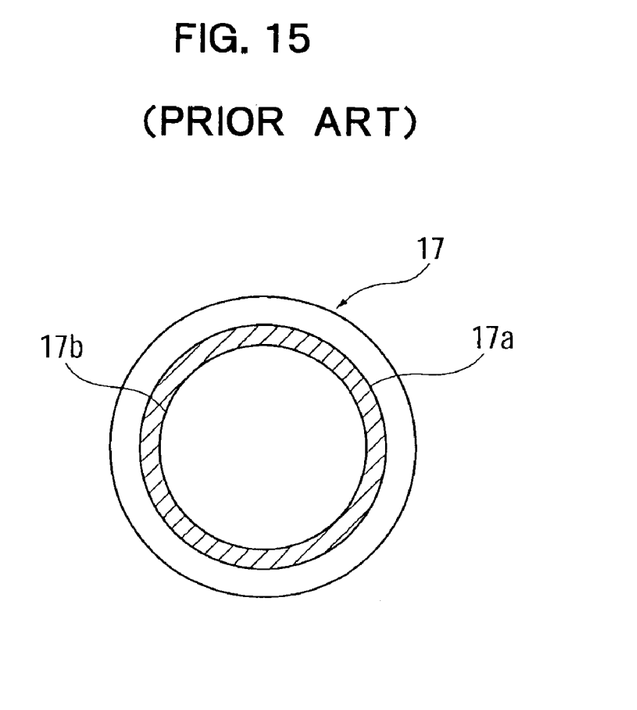
FIG. 15 is a cross-sectional view taken along line XV-XV of FIG. 14.
Figure 16:
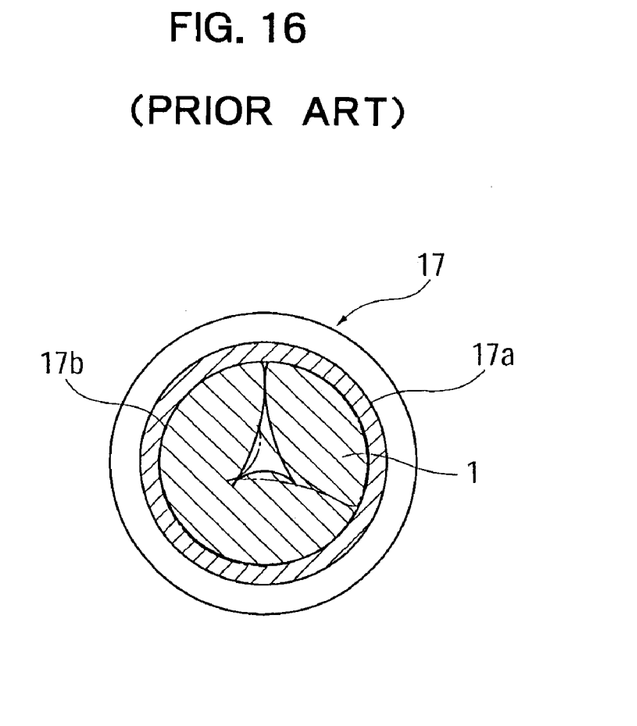
FIG. 16 is a cross-sectional view showing how an intraocular lens is deformed in the insertion tube of FIG. 14, and used for describing operation of the device of FIG. 12.

FIG. 12 is a partially cutaway perspective view of a conventional insertion device for a deformable intraocular lens. FIG. 14 is an enlarged perspective view of an insertion end portion of the insertion device. FIG. 15 is a cross sectional view taken along line XV-XV of FIG. 14. FIG. 16 is an enlarged perspective view of the insertion end portion of the insertion device which is used for description of operation.

In FIG. 12, reference numeral 11 denotes a device body; 12 denotes a push rod; 13 denotes a male-thread shaft; and 14 denotes a push-out mechanism.

Figure 13:
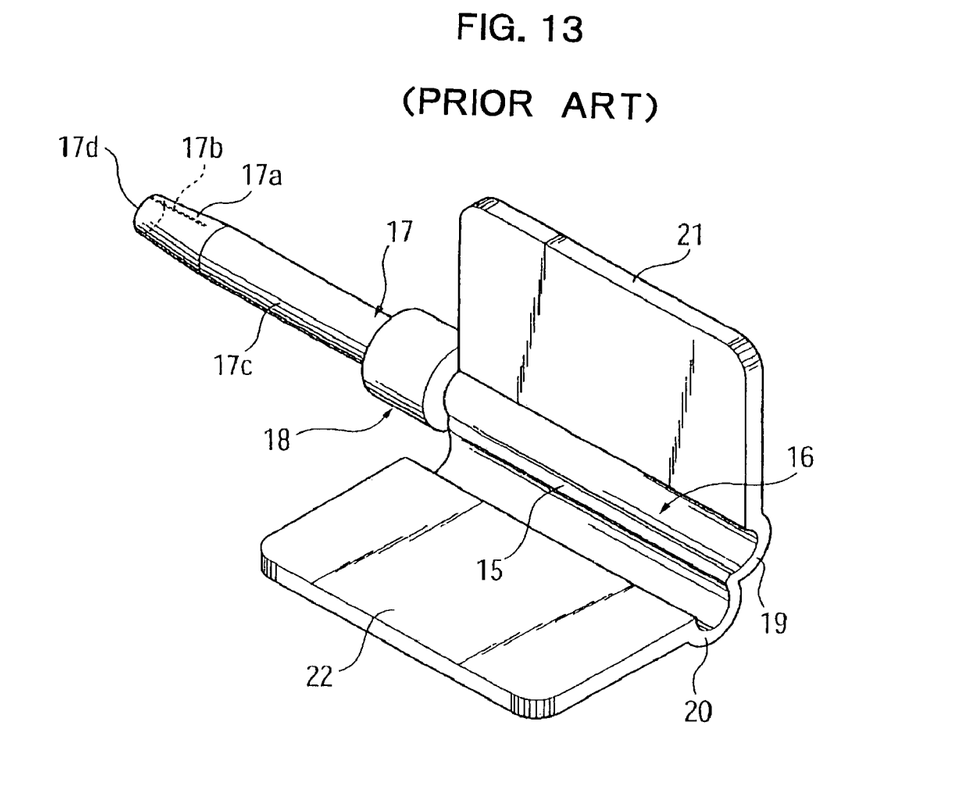
FIG. 13 is an enlarged perspective view of the enclosing member of FIG. 12.

Reference numeral 18 denotes an enclosing member. As shown in FIG. 13, the enclosing member 18 is provided with a lens receiving section 16 having a hinge portion 15. An insertion tube 17 projects from the front end of the lens receiving section 16. A tapered insertion end portion 17a of the insertion tube 17 has an axially extending slit 17b. The lens receiving section 16 has a stationary half sleeve 19 and a movable half sleeve 20, whose lower edge portions are connected together by means of the hinge portion 15. Stationary and movable press plates 21 and 22 project from the stationary and movable half sleeves 19 and 20, respectively.

The conventional insertion device having the above-described structure is used as follows. The intraocular lens 1 is placed on the lens receiving section 16 of the enclosing member 18 and is folded into a smaller size before being loaded onto the insertion device body 11.

Upon completion of loading of the intraocular lens 1, the male-thread shaft 13 of the intraocular-lens insertion device is rotated in order to screw-feed the push rod 12. As a result, a process of inserting the intraocular lens 1 into the eye starts.

The intraocular lens 1 is gradually pushed forward by the tip end of the push rod 12. When the intraocular lens 1 reaches the tapered insertion end portion 17a of the insertion tube 17, the axially extending slit 17b of the insertion end portion 17a opens gradually. As a result, stresses in the optical portion 2 of the intraocular lens 1, which has been folded at the base end portion 17c of the insertion tube 17, are gradually released at the insertion end portion 17a. Subsequently, the intraocular lens 1 is inserted into the eye from an open end 17d of the insertion tube 17.

The slit 17b holds the optical portion 2 of the intraocular lens 1 while sandwiching it, to thereby prevent abrupt ejection of the intraocular lens 1 into the eye. In addition, although the slit 17b releases stresses from the intraocular lens 1, the intraocular lens 1 is retained at the insertion end portion 17a, because cut surfaces located above and below the slit 17b hold the intraocular lens 1 from both sides thereof. Moreover, the slit 17b can control insertion speed of the intraocular lens 1 to match advancement speed of the push rod 12.

However, in the conventional insertion device, the insertion tube is not configured to prevent rotational movement about the insertion tube axis of an intraocular lens that is contained therein in a folded condition. As a result, as shown in FIG. 16, in some cases, the intraocular lens 1 within the insertion tube 17 may move unexpectedly in a rotational direction along the inner wall surface of the insertion tube 17 as represented by the dot-and-dash line.

Such an unexpected rotational movement of the folded intraocular lens within the insertion tube changes a positional relation between the folded intraocular lens and the slit formed in the insertion end portion of the insertion tube. As a result, the intraocular lens fails to project from the insertion end portion of the insertion tube in a desired condition. Accordingly, difficulty arises in controlling insertion of the intraocular lens with consistent repeatability in terms of insertion orientation and insertion speed. Therefore, a surgical procedure for implantation of the intraocular lens has required a great deal of skill.

Meanwhile, in order to prevent such an unexpected rotational movement of the intraocular lens, the assignee of the present invention has proposed an insertion device which includes an insertion tube having a guide portion that extends parallel to the axis of the insertion tube.

SUMMARY OF THE INVENTION

In view of the foregoing, an object of the present invention is to provide an insertion device for a deformable intraocular lens configured such that, during an operation of inserting the intraocular lens into the eye, an intraocular lens is prevented from undergoing an unexpected rotational movement about the insertion tube axis and is intentionally caused to move rotationally in a desired direction, thereby maintaining consistent movement and stable insertion speed of the intraocular lens and its support portions and providing a safer procedure of inserting the intraocular lens into the eye.

In order to achieve the above-described object, the present invention provides an intraocular-lens insertion device for deforming a deformable intraocular lens to a smaller size and inserting the intraocular lens into an eye via an insertion tube, wherein the insertion tube has an inner wall which is shaped to cause the deformable intraocular lens to move rotationally about an insertion tube axis by a predetermined angle in the course of axial advancing movement of the lens.

The insertion tube may be formed in such a manner that the inner wall has an elliptical transverse cross section, and the directions of the major and minor axes of the ellipse gradually rotate about the insertion tube axis toward a tip end of the insertion tube, so that the deformable intraocular lens moves rotationally about the insertion tube axis by a predetermined angle in the course of axial advancing movement of the lens.

Alternatively, the insertion tube may be formed in such a manner that the inner wall of the insertion tube has a guide portion extending along the insertion tube axis, and angular position of the guide portion with respect to the insertion tube axis gradually changes toward a tip end of the insertion tube, so that the deformable intraocular lens moves rotationally about the insertion tube axis by a predetermined angle in the course of axial advancing movement of the lens. In this case, the guide portion may be a rail provided on the inner wall and having a rectangular transverse cross section, or a groove formed on the inner wall.

By virtue of the above-described inner wall shape of the insertion tube, the folded intraocular lens can be moved rotationally by a predetermined angle about the insertion tube axis in the course of passage through the insertion tube, thereby implementing a consistent insertion operation. Accordingly, a surgical procedure for implantation of the intraocular lens does not require a particularly high level of skill.

The above-described guide portion prevents unexpected circular rotation of an intraocular lens about the insertion tube axis and intentionally causes the intraocular lens to move rotationally in a desired direction, thereby maintaining consistent movement and stable insertion speed of the intraocular lens and its support portions and providing a safer procedure of inserting the intraocular lens into the eye.

BRIEF DESCRIPTION OF THE DRAWINGS

Various other objects, features and many of the attendant advantages of the present invention will be readily appreciated as the same becomes better understood by reference to the following detailed description of the preferred embodiments when considered in connection with the accompanying drawings, in which.

DETAILED DESCRIPTION OF PREFERRED EMBODIMENTS

Embodiments of the present invention will be described with reference to the accompanying drawings.

First Embodiment

An intraocular-lens insertion device according to a first embodiment of the present invention will be described with reference to FIG. 1A.

Figure 1A:
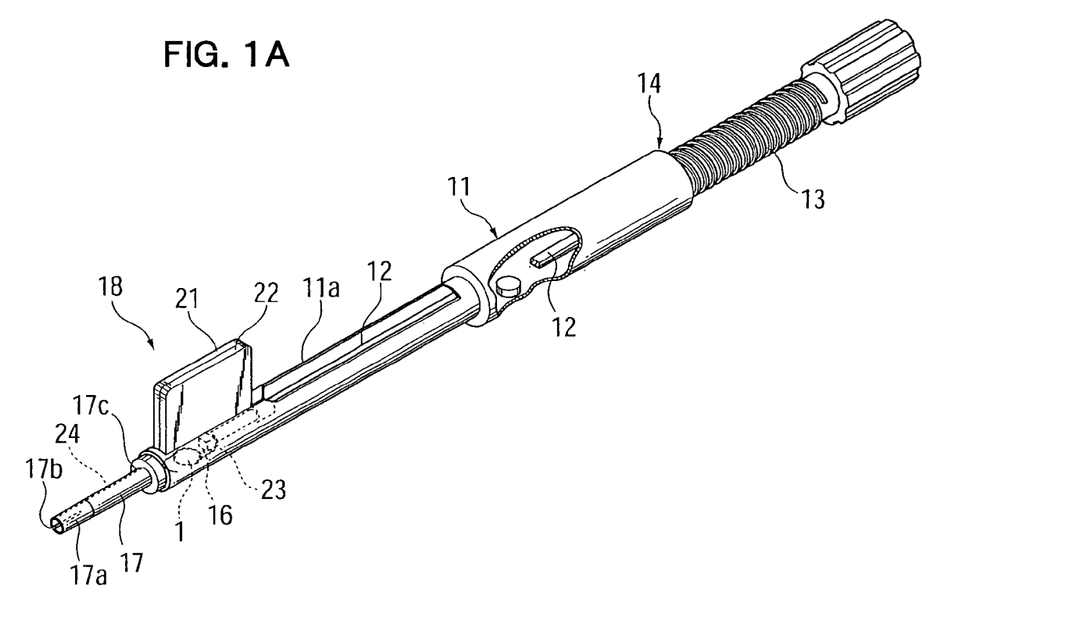
FIG. 1A is a partially cutaway perspective view of an intraocular-lens insertion device according to a first embodiment of the present invention.

As shown in FIG. 1A, the intraocular-lens insertion device of the present embodiment includes a generally cylindrical, tubular device body 11; a push rod 12 fitted into the device body 11; a push-out mechanism 14 including a male-thread shaft 13 in screw-engagement with a female thread (not shown) formed on the inner wall surface of the device body 11; and an enclosing member 18, which has a lens receiving section 16 having a hinge portion 15, and an insertion tube 17 projecting forward from the lens receiving section 16.

An attachment groove 11a is formed in an upper portion of a tip end portion of the device body 11. The enclosing member 18 is loaded into the device body 11 via the groove 11a.

The push rod 12 is rotatably connected, at its one end, to the male-thread shaft 13 and is supported by the device body 11 in such a manner that its rotation with respect to the device body 11 is restricted.

Figure 1B:
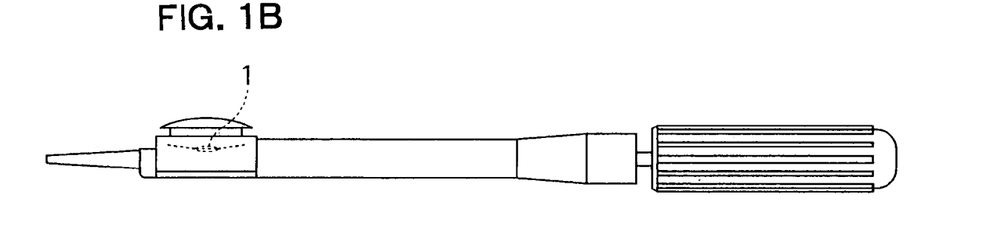
FIG. 1B is a side view of a modification of the first embodiment in which an intraocular lens is held beforehand.

FIG. 1B shows a modification of the first embodiment shown in FIG. 1A. In the intraocular-lens insertion device of FIG. 1B, an intraocular lens 1 is held therein beforehand as in the case of an intraocular-lens insertion device that had been proposed by the assignee of the present invention and disclosed in Japanese Patent Application Laid-Open (kokai) No. 2001-104347.

Even when applied to the configuration shown in FIG. 1B, the present invention yields the same effect as in the case of the first embodiment shown in FIG. 1A. Therefore, only the first embodiment will be representatively described below.

Figure 2:
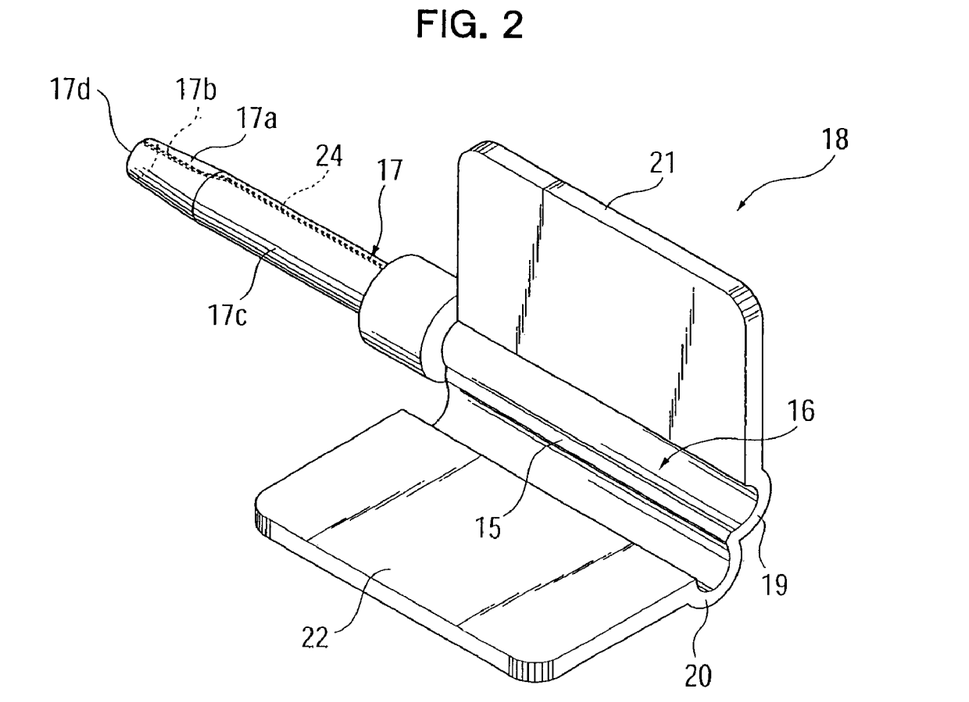
FIG. 2 is an enlarged perspective view of the enclosing member of FIG. 1A.
Figure 3:
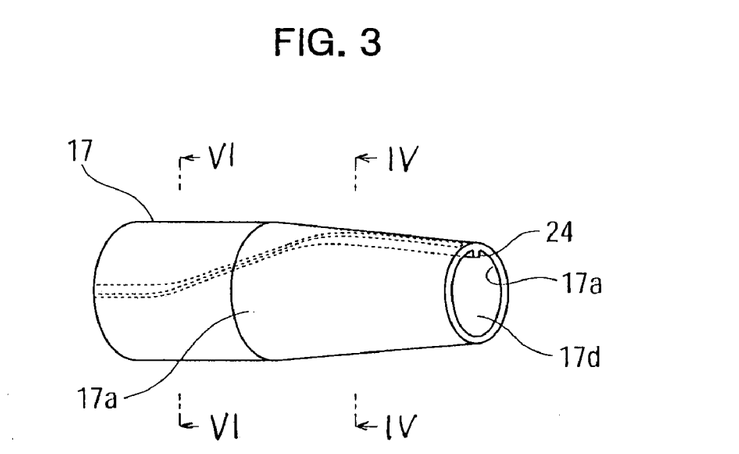
FIG. 3 is an enlarged perspective view of the insertion end portion of FIG. 1A.
Figure 4:
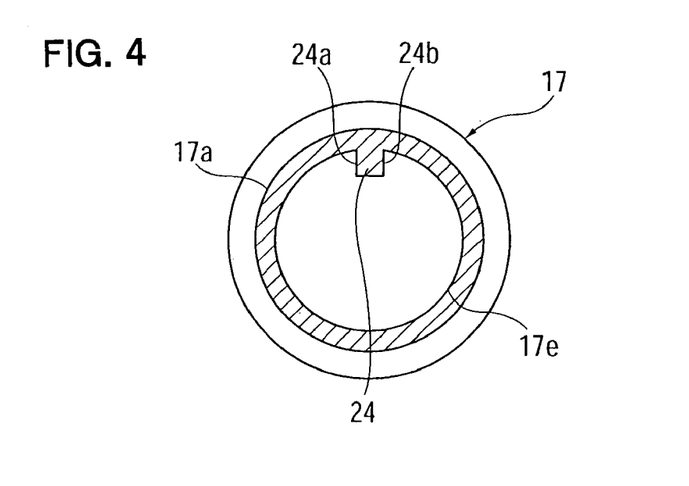
FIG. 4 is a cross-sectional view taken along line IV-IV of FIG. 3.

As shown in FIG. 2, the lens receiving section 16 of the enclosing member 18 has a stationary half sleeve 19 and a movable half sleeve 20, whose lower edge portions are connected together by means of the hinge portion 15. The stationary half sleeve 19 is fixedly provided at the rear end of the insertion tube 17. The movable half sleeve 20 is located close to the rear end of the insertion tube 17 and can be opened and closed with respect to the stationary half sleeve 19. Stationary and movable press plates 21 and 22 project from the stationary and movable half sleeves 19 and 20, respectively.

The movable half sleeve 20, the hinge portion 15, and the movable press plate 22 constitute an open/close mechanism. When the open/close mechanism is closed, the movable press plate 22 comes into contact with the stationary press plate 21, so that the stationary half sleeve 19 and the movable half sleeve 20 form a tube that is coaxial with the insertion tube 17. When the movable press plate 22 is closed while the intraocular lens 1 is placed in the lens receiving section 16, the intraocular lens 1 is folded to a smaller size.

The insertion tube 17 has an internal diameter at its base end portion 17c which is equal to that of the tube which is formed by the stationary half sleeve 19 and the movable half sleeve 20 upon mutual contact. The insertion tube 17 has a tapered insertion end portion 17a which extends from the base end portion 17c.

The structure described above is substantially identical with that disclosed in Japanese Patent Application Laid-Open (kokai) No. 05-103803 (prior art).

As shown in FIGS. 3 to 6, the intraocular-lens insertion device according to the first embodiment has a rail-like guide portion 24, which is formed on an inner wall surface 17e of the insertion tube 17 and projects radially inward, more specifically, toward the axis of the insertion tube 17, which may be referred to as "insertion tube axis." The guide portion 24 causes the folded intraocular lens 1 to move rotationally about the insertion tube axis by a predetermined angle while the folded intraocular lens 1 is pushed forward. The guide portion 24 is formed integrally on the insertion tube 17, and has a rectangular cross section. In a transitional region between the base end portion 17c and the insertion end portion 17a, the guide portion 24 extends while changing its position rotationally about the axis of the insertion tube 17 by a predetermined angle.

The intraocular lens 1 shown in FIG. 10 has the circular optical portion 2 and two symmetrically disposed supports 3. The circular optical portion 2 is made of an elastic material having predetermined memory characteristics. The supports 3 are made of a material different from that of the optical portion 2.

The intraocular-lens insertion device according to the first embodiment including the insertion end portion 17a having the above-described structure is used as follows. First, the enclosing member 18 is removed from the attachment groove 11a of the device body 11. Subsequently, the movable press plate 22 and the movable half sleeve 20 of the enclosing member 18 are opened; and the optical portion 2 of the intraocular lens 1 is placed on the hinge portion 15 of the lens receiving section 16 while a predetermined clearance is formed therebetween, such that one support 3 of the intraocular lens 1 is located on the front side and the other support 3 of the intraocular lens 1 is located on the rear side. Subsequently, the movable press plate 22 and the movable half sleeve 20 are closed and brought into contact with the stationary press plate 21 and the stationary half sleeve 19, respectively, whereby the optical portion 2 is folded in half within the half sleeves 19 and 20 to thereby be deformed to a smaller size. Subsequently, the enclosing member 18 is attached to the attachment groove 11a of the device body 11.

After the insertion end portion 17a of the insertion tube 17 is inserted into an incision formed in the eye, the male-thread shaft 13 of the push-out mechanism 14 is rotated. As a result, a tip end portion 23 of the push rod 12 pushes the optical portion 2 of the intraocular lens 1 into the insertion end portion 17a of the insertion tube 17, whereby the intraocular lens 1 is gradually ejected into the eye.

Figure 5:
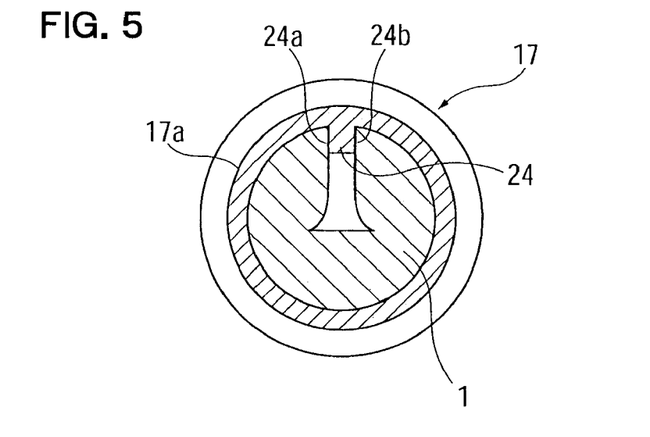
FIG. 5 is a cross-sectional view showing how an intraocular lens is deformed in the insertion tube of FIG. 3, and used for describing operation of the device of FIG. 1A.
Figure 6:
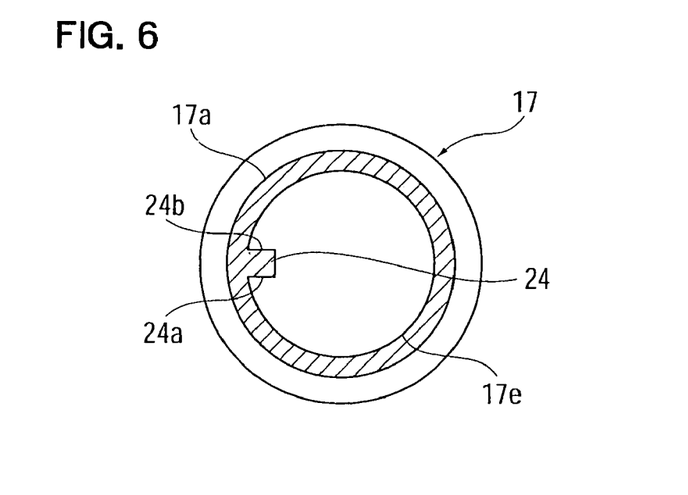
FIG. 6 is a cross-sectional view taken along line VI-VI of FIG. 3.

When the intraocular lens 1 arrives at the insertion end portion 17a in the course of movement, as shown in FIG. 5, opposite end portions of the folded intraocular lens 1 nip therebetween the guide portion 24 formed on the inner wall surface 17e of the insertion tube 17 while being in contact with corresponding opposite side surfaces 24a and 24b of the guide portion 24. Accordingly, the folded intraocular lens 1 moves along the guide portion 24 to thereby move rotationally about the insertion tube axis. As a result, while moving rotationally, the folded intraocular lens 1 is pushed forward by means of the tip end portion 23 of the push rod 12.

The tip end portion 23 of the push rod 12 has a sufficient clearance portion in order to avoid contact with the guide portion 24, which projects radially inward from the inner wall of the insertion tube 17.

The intraocular lens 1 is pushed forward in the insertion tube 17 while moving rotationally about the insertion tube-axis and is ejected from an open end 17d of the insertion end portion 17a.

Thus, the intraocular-lens insertion device according to the first embodiment can consistently control the insertion orientation and insertion speed of the intraocular lens 1 as well as the ejection angle of the supports 3 within the eye.

Second Embodiment

Figure 7:
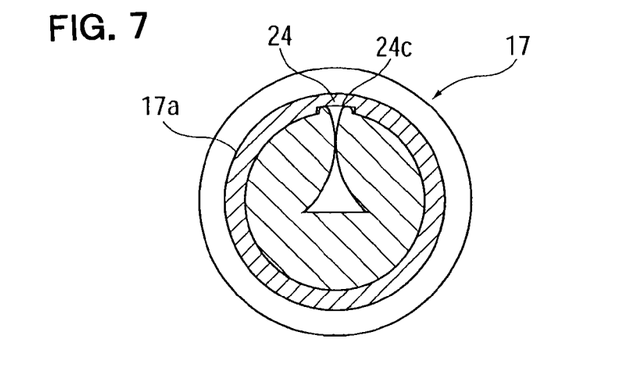
FIG. 7 is a cross-sectional view showing how an intraocular lens is deformed in the insertion tube of an intraocular-lens insertion device according to a second embodiment of the present invention, and used for describing operation of the device of the second embodiment.

FIG. 7 shows the guide portion 24 of an intraocular-lens insertion device according to a second embodiment of the present invention.

As shown in FIG. 7, the guide portion 24 is a groove 24c that is formed on the inner wall surface of the insertion tube 17. The groove 24c faces the axis of the insertion tube 17; i.e., the insertion tube axis, and axially extends. As in the case of the first embodiment, in the transitional region between the base end portion 17c and the insertion end portion 17a, the groove 24c changes its position rotationally about the axis of the insertion tube 17 by a predetermined angle. The intraocular lens 1 moves along the groove 24c while being guided by the groove 24c by virtue of its restoration force, and thus can be moved rotationally about the insertion tube axis. The intraocular-lens insertion device of the second embodiment is effectively used, particularly with a thick intraocular lens.

Third Embodiment

Figure 8:
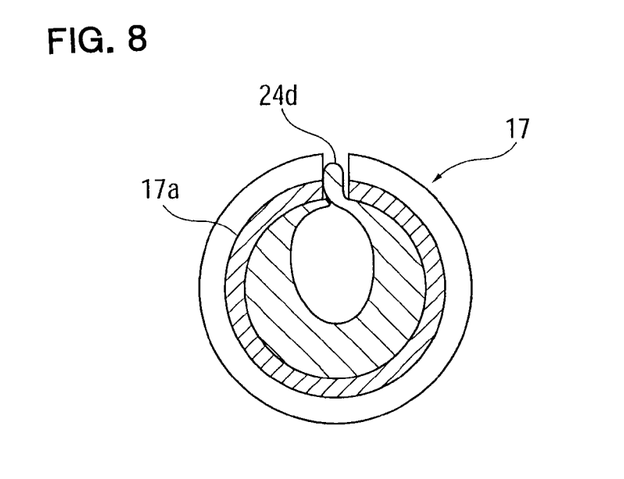
FIG. 8 is a cross-sectional view showing how an intraocular lens is deformed in the insertion tube of an intraocular-lens insertion device according to a third embodiment of the present invention, and used for describing operation of the device of the third embodiment.

FIG. 8 shows the guide portion 24 of an intraocular-lens insertion device according to a third embodiment of the present invention.

As shown in FIG. 8, the guide portion 24 is a groove 24d that is formed in the insertion tube 17 in such a manner as to extend from the inner wall surface to the outer wall surface thereof, and axially extends. As in the case of the first embodiment, in the transitional region between the base end portion 17c and the insertion end portion 17a, the groove 24d changes its position rotationally about the axis of the insertion tube 17 by a predetermined angle. The intraocular lens 1 moves along the groove 24d while its peripheral edge is guided by the groove 24d, and thus can be moved rotationally about the insertion tube axis. The intraocular-lens insertion device of the third embodiment is effectively used, particularly with a thin intraocular lens.

Fourth Embodiment

Figure 9:
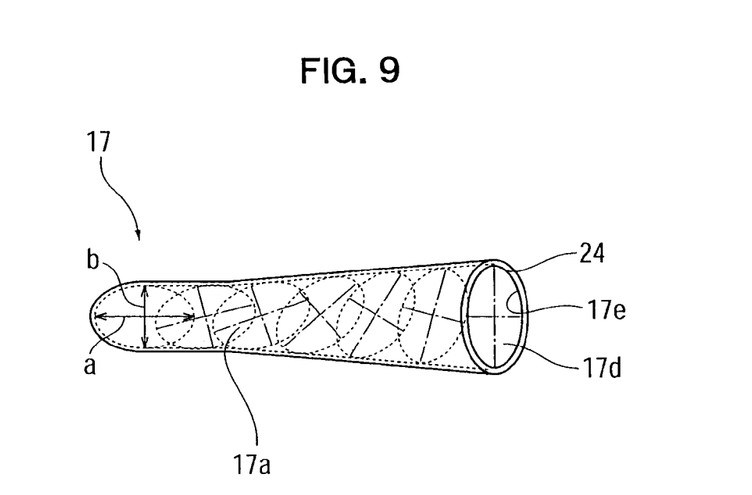
FIG. 9 is an enlarged perspective view of the insertion end portion of an intraocular-lens insertion device according to a fourth embodiment of the present invention.

FIG. 9 shows the insertion tube 17 of an intraocular-lens insertion device according to a fourth embodiment of the present invention.

The insertion tube 17 of FIG. 9 does not have a guide portion, but has an inner wall shape that can cause the intraocular lens 1 to move rotationally about the insertion tube axis. As shown in FIG. 9, the insertion tube 17 has an elliptical cross section having a major diameter a and a minor diameter b. The peripheral edge of the intraocular lens 1 comes into contact with longer side portions of the insertion tube 17, which portions extend along the major axis of the ellipse. The insertion tube 17 is formed in such a manner that the directions of the major and minor axes of the ellipse gradually change by a predetermined angle over the length of the insertion tube 17, or over a portion of the length of the insertion tube 17. Therefore, when the intraocular lens 1 moves through the insertion tube 17, the inner wall surface of the insertion tube 17 causes the intraocular lens 1 to rotate or move rotationally about the insertion tube axis.

The above embodiments are described while mentioning an intraocular-lens insertion device in which a slit is not formed in the insertion end portion 17a of the insertion tube 17. However, the present invention is not limited thereto, but is applicable to an intraocular-lens insertion device in which a slit or cut is formed in an insertion end portion of the insertion tube, such as those disclosed in Japanese Patent Application Laid-Open (kokai) Nos. 5-103803 and 8-38542.

The first embodiment is described while mentioning the guide portion 24 that is a projection formed integrally on the inner wall surface 17e of the insertion tube 17. However, the present invention is not limited thereto. The guide portion 24 may be a separately formed, elongated member. The elongated member may be joined to the inner wall surface 17e by application of heat or by use of adhesive.

The third embodiment is described while mentioning the insertion tube which has an elliptical cross section. However, the present invention is not limited thereto so long as the insertion tube has a noncircular cross section which causes the intraocular lens to move rotationally about the insertion tube axis by a predetermined angle in the course of its axial movement.

Obviously, numerous modifications and variations of the present invention are possible in light of the above teachings. It is therefore to be understood that within the scope of the appended claims, the present invention may be practiced otherwise than as specifically described herein.

What is claimed is:

1. An intraocular-lens insertion device comprising an insertion tube and a lens pusher for ejecting a deformable intraocular lens from said insertion tube, said insertion tube having an inner wall shaped to cause the entire deformable intraocular lens to move rotationally about an insertion tube axis by a predetermined angle in the course of axial advancing movement of the lens.

2. An intraocular-lens insertion device according to claim 1, wherein the inner wall has an elliptical transverse cross section having major and minor axes, and the directions of the major and minor axes of the ellipse gradually rotate about the insertion tube axis toward a tip end of the insertion tube, so that the deformable intraocular lens moves rotationally about the insertion tube axis by a predetermined angle in the course of axial advancing movement of the lens.

3. An intraocular-lens insertion device according to claim 1, wherein the inner wall of the insertion tube has a guide portion extending along the insertion tube axis, and angular position of the guide portion with respect to the insertion tube axis gradually changes toward a tip end of the insertion tube, so that the deformable intraocular lens moves rotationally about the insertion tube axis by a predetermined angle in the course of axial advancing movement of the lens.

4. An intraocular-lens insertion device according to claim 3, wherein the guide portion is a rail which protrudes inwardly from said inner wall, said rail having a rectangular transverse cross section.

5. An intraocular-lens insertion device according to claim 3, wherein the guide portion is a groove formed on the inner wall.

6. An intraocular-lens insertion device according to claim 5, wherein the groove extends to an outer surface of the insertion tube.

* * * * *